(12) United States Patent
Ho et al.

(10) Patent No.: US 9,111,473 B1
(45) Date of Patent: Aug. 18, 2015

(54) INPUT SYSTEM

(75) Inventors: Harvey Ho, Mountain View, CA (US);
Xiaoyu Miao, Sunnyvale, CA (US);
Nathan Pletcher, Mountain View, CA (US)

(73) Assignee: Google Inc., Mountain View, CA (US)

( * ) Notice: Subject to any disclaimer, the term of this patent is extended or adjusted under 35 U.S.C. 154(b) by 152 days.

(21) Appl. No.: 13/594,291

(22) Filed: Aug. 24, 2012

(51) Int. Cl.
*G09G 5/00* (2006.01)
*A61B 3/113* (2006.01)

(52) U.S. Cl.
CPC ......................................... *G09G 5/00* (2013.01)

(58) Field of Classification Search
CPC ............. G09G 5/00; G09G 5/10; G06F 7/00; G02C 7/04; A61B 3/113
USPC ........... 345/157; 351/160 R, 159.03; 348/143
See application file for complete search history.

(56) References Cited

U.S. PATENT DOCUMENTS

| | | |
|---|---|---|
| 3,958,560 A | 5/1976 | March |
| 4,014,321 A | 3/1977 | March |
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Andrew Sasinowski
(74) *Attorney, Agent, or Firm* — Blakely Sokoloff Taylor & Zafman LLP (57) ABSTRACT

Apparatus, systems and methods that facilitate eye tracking using a contact lens are provided. In some aspects, the contact lens includes: a substrate; an antenna, disposed on or within the substrate, that harvests radio frequency energy; an integrated circuit, disposed on or within the substrate, that receives power from the antenna; and electrical components, disposed on or within the substrate, that determine motion of an eye over which the contact lens is placed, and perform tracking of the eye based, at least, on the motion. For example, the motion of the eye can be determined based on telemetry components fabricated on or within a substrate of the contact lens. In some aspects, the contact lens can include light emitters that radiate light in a direction of the gaze of the wearer of the contact lens. A heads-up device can perform eye tracking based on the direction of the light beams.

9 Claims, 9 Drawing Sheets

(56) References Cited

U.S. PATENT DOCUMENTS

| | | |
|---|---|---|
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A * | 7/2000 | Ferraz ............... 340/575 |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 * | 3/2006 | Blum et al. ............... 351/159.03 |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 7,970,477 B2 * | 6/2011 | Loeb et al. ............... 607/48 |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 * | 1/2010 | Amirparviz et al. ............... 345/7 |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0045571 A1 * | 2/2010 | Yamamoto ............... 345/8 |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | M ller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1617757 | 1/2006 |

(56) References Cited

FOREIGN PATENT DOCUMENTS

| | | |
|---|---|---|
| EP | 1818008 | 8/2007 |
| EP | 1947501 | 7/2008 |
| EP | 2457122 | 5/2012 |
| WO | 95/04609 | 2/1995 |
| WO | 0116641 | 3/2001 |
| WO | 01/34312 | 5/2001 |
| WO | 03065876 | 8/2003 |
| WO | 2004/060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Ho et al., "Contact Lens With Integrated Inorganic Semiconductor Devices," MEMS 2008. IEEE 21st International Conference on. IEEE, 2008., pp. 403-406.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Saeedi, E. et al., "Self-assembled crystalline semiconductor optoelectronics on glass and plastic," J. Micromech. Microeng., 2008, pp. 1-7, vol. 18.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Selner, et al., "Novel Contact Lens Electrode Array for Multi-electrode Electroretinography (meERG)," IEEE, 2011, 2 pages.

Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3μW Wirelessly Powered CMOS Glucose Sensor for an Active Contact Lens," 2011 IEEE International Solid-State Circuits Conference, Session 2, Feb. 21, 2011, 3 pages.

Lončar, et al., "Design and Fabrication of Silicon Photonic Crystal Optical Waveguides," Journal of Lightwave Technology, Oct. 2000, vol. 18, No. 10, pp. 1402-1411.

Liu, et al., "Miniature Amperometric Self-Powered Continuous Glucose Sensor with Linear Response," Analytical Chemistry, 7 pages.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Baxter, "Capacitive Sensors," 2000, 17 pages.

Lingley, et al., "A Single-Pixel Wireless Contact Lens Display," Journal of Micromechanics and Microengineering, 2011, 9 pages.

"Polyvinylidene fluoride," Wikipedia, http://en.wikipedia.org/wiki/Polyvinylidene_fluoride, Last accessed Mar. 30, 2012, 4 pages.

Murdan, "Electro-responsive drug delivery from hydrogels," Journal of Controlled Release, 2003, vol. 92, pp. 1-17.

(56) References Cited

OTHER PUBLICATIONS

Haders, "New Controlled Release Technologies Broaden Opportunities for Ophthalmic Therapies," Drug Delivery Technology, Jul./Aug. 2009, vol. 8, No. 7, pp. 48-53.

Singh, et al., "Novel Approaches in Formulation and Drug Delivery using Contact Lenses," Journal of Basic and Clinical Pharmacy, May 2011, vol. 2, Issue 2, pp. 87-101.

"Contact Lenses: Look Into My Eyes," The Economist, Jun. 2, 2011, http://www.economist.com/node/18750624/print, Last accessed Mar. 13, 2012, 8 pages.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.

Unpublished U.S. Appl. No. 13/240,994, Titled "See-Through Display With Infrared Eye-Tracker," Filed Sep. 22, 2011, 38 pages.

Unpublished U.S. Appl. No. 13/209,706, Titled "Optical Display System and Method with Gaze Tracking," Filed Aug. 15, 2011, 30 pages.

Liu et al., "Miniature Amperometric Self-Powered Continuous Glucose Sensor with Linear Response," Analytical Chemistry, 2012, pp. 3403-3409, vol. 84.

* cited by examiner

INPUT SYSTEM

TECHNICAL FIELD

This disclosure generally relates to facilitation of eye tracking using contact lenses.

BACKGROUND

Traditionally, eye tracking relies on using a camera that faces an eye and detects eye motion. For example, eye tracking using a heads-up device typically requires a camera facing the eye. Further, current eye tracking systems using cameras typically require line-of-sight to the eye and illumination systems to gather information about gaze position of the eye. Unfortunately, these types of systems are typically bulky and difficult to implement as lightweight, small form factor, wearable devices.

DETAILED DESCRIPTION

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

Micro-fabrication describes the process of fabrication of structures that are micrometer-sized and smaller. Micro-fabrication involves a multi-step process that includes microlithography, doping, thin films, etching, bonding and polishing. Advances in micro-fabrication have enabled use of numerous different types of components for small-scale devices and circuits. For example, accelerometers and gyroscopes can be designed employing micro-fabrication techniques. These devices can be employed in contact lens circuits to enable tracking of movement and/or position of the eye.

Optical communication is a form of telecommunication that employs light as a transmission medium. Optical systems can also be advantageous as an unobtrusive and efficient method for tracking position and/or movement of eyes.

Micro-fabrication techniques can be employed to provide components that can receive and/or transmit light from or to the contact lens. For example, optical waveguides can be designed and fabricated that incorporate two-dimensional (2-D) photonic crystal geometry for lateral confinement of light, and total internal reflection for vertical confinement. Square, triangular or other suitable photonic crystal lattices can be utilized. In an aspect, a three-dimensional (3-D) finite-difference time-domain (FDTD) can be used to find design parameters of the photonic crystal and to calculate dispersion relations for guided modes in a waveguide structure. In an aspect, the waveguides can be fabricated so as to improve confinement in a particular direction and symmetry properties of the structure. High-resolution fabrication can provide for different types of bends and optical cavities within the waveguides. The optical waveguides can facilitate directing light to and from components of the contact lens, and facilitate mitigation of losses associated with dispersion of light.

Multiple optical transmitters can be situated on the contact lens and multiplex and/or modulate multiple optical signals (e.g., using different sources as well as different colors, or wavelength frequencies) in order to enhance encoding of data (e.g., data sensed on the contact lens). For example, optical signals of different wavelengths or strengths can communicate different information.

Multiple optical receivers/sensors can be situated on the contact lens to enhance determination of position of an eye. For example, the optical receivers/sensors can receive signals of different strengths based on location of the receiver/sensor and position of the eye. Accordingly, different signals can be evaluated and determination of position of the eye can be made.

Sensors can alternately be employed on a device external to the contact lens for determination of position of the eye. For example, CMOS-based sensors and CCD-based sensors receive light at an array of one or more cells. The received light is then converted into electrons. The accumulated charge resultant from conversion of light in each cell into electrons is determined CCD-based sensors determine accumulated charge by transporting charge across a chip and reading charge at a single location in the array after an analog-to-digital (A/D) converter converts the value at each cell into a digital value. CMOS-based sensors determine accumulated charge by employing a transistor at each cell to amplify and transport charge at each cell. While CCD-based sensors advantageously transport charge without distortion and correspondingly, high fidelity sensing making low-noise imaging possible, CMOS-based sensors have greater flexibility because charge at each cell is read individually. Additionally, CMOS-based sensors tend to consume less power than CCD-based sensors.

Apparatus, systems and methods disclosed herein relate to facilitation of eye tracking. In some of these aspects, a contact lens is employed. For example, a contact lens can include: a substrate and a circuit disposed on or within the substrate. The circuit can include: an antenna configured to harvest radio frequency energy; an integrated circuit configured to receive power from the antenna; and one or more electrical components (e.g., telemetry components) configured to determine motion of an eye over which the contact lens is placed, and perform tracking of the eye based, at least, on the motion.

As another example, in some aspects, a contact lens can include one or more light emitters configured to radiate light beams. The light beams can radiate light in a direction corresponding to the direction of a gaze of the wearer of the contact lens. The radiated light beams can be detected by a heads-up device external to and in geographic proximity of the contact lens. The heads-up device can determine a direction of a gaze of the wearer of the contact lens based, at least, on the direction of the light beams.

As another example, another contact lens can include: a substrate; and a circuit disposed on or within the substrate. The circuit can include a multi-antenna system, disposed on or within the substrate: configured to receive a signal at a plurality of antennas of the multi-antenna system; and configured to determine respective signal strength information for the signal received at the plurality of antennas. The circuit can determine the orientation of the contact lens based, at least, on the respective signal strength information at the plurality of antennas.

As another example, a system can include a heads-up device. The heads-up device can include: a light source configured to emit light; a waveguide configured to direct the light towards an eye in geographic proximity to the heads-up device; a light detector configured to receive reflected light from the eye; and a circuit configured to determine a direction of a gaze of the eye based, at least, on the reflected light. Regarding the reflected light, in some aspects, the display can have information on the light projected towards the eye (e.g., the color of the light, intensity of the light, etc.). The reflected light can be received back at the sensor of the heads-up device in a very short time such that the sensor should know what light received is the reflected signal and what light received is environmental noise that is coupled into the waveguide.

One or more of the aspects can advantageously facilitate eye tracking utilizing an efficient, lightweight and/or small form factor (e.g., a contact lens).

Figure 1:
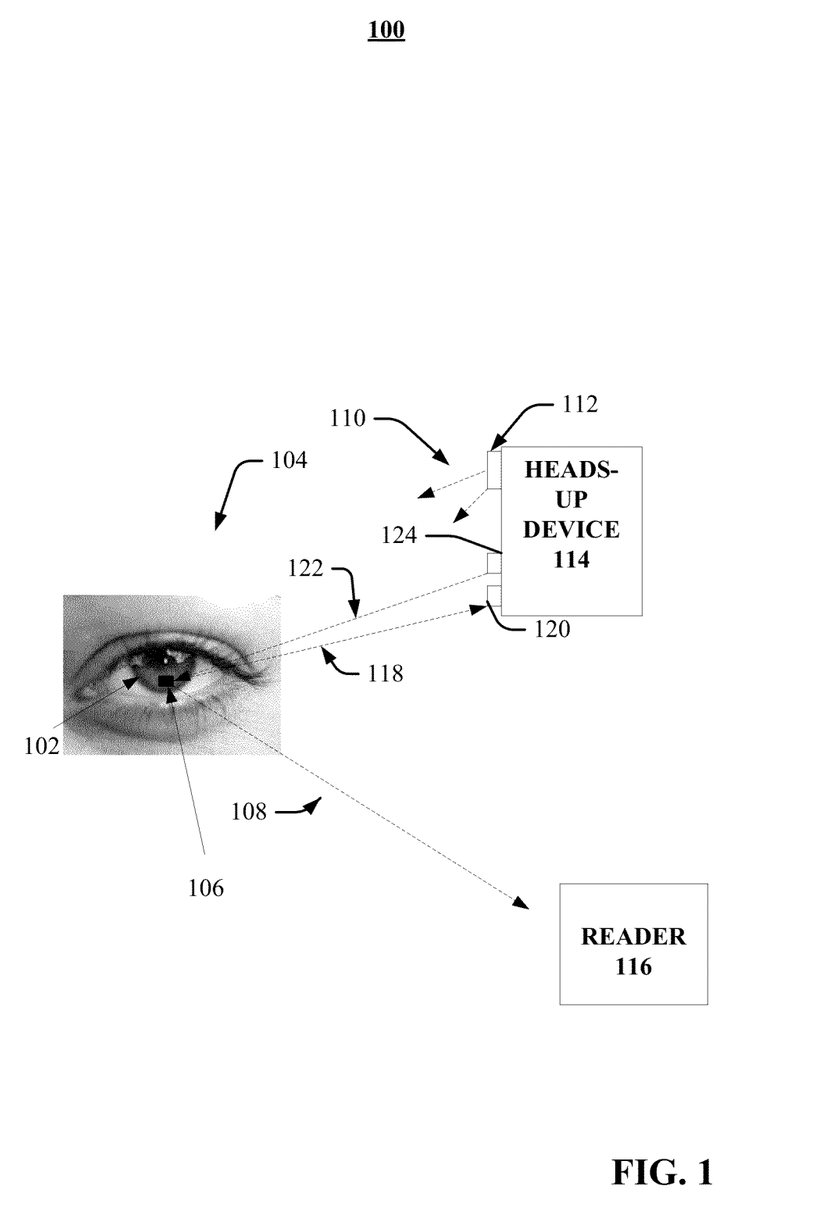
FIG. 1 is an illustration of a block diagram of an exemplary non-limiting system that facilitates eye tracking employing a contact lens in accordance with aspects described herein.

FIG. 1 is an illustration of a block diagram of an exemplary non-limiting system that facilitates eye tracking via a contact lens in accordance with aspects described herein. The system 100 can include a contact lens 102 covering at least a portion of an eye 104 of wearer of the contact lens 102. The contact lens can include a substrate (not shown), and a circuit 106 disposed on or within a substrate of the contact lens 102.

A number of different systems can be employed to facilitate eye tracking. For example, in some aspects, the circuit 106 can determine motion of the eye 104 and/or perform tracking of the eye 104 based on motion. To determine motion, for example, the circuit 106 can generate telemetry associated with motion of the eye 104. The telemetry can include information indicative of angular displacement, position, movement and/or acceleration of the eye. For example, a gyroscope on the contact lens 102 can provide angular rate of movement of the eye. The data representative of angular rate can be integrated over time to determine amount of angular displacement that has occurred based on movement of the eye. In some aspects, history of past angular displacement data can be collected. This information can be employed to map out a boundary of where the eye goes (e.g., maximum displacement means the eyeball has fully looked up). The set of data can be used to compute absolute position. An accelerometer can measure acceleration of the eye.

Another approach to eye tracking can employ use of a waveguide on a heads-up device 114. For example, the waveguide can have a reciprocal optical system with an optics module capable of producing light as well as sensing light levels received at the optics module. The light levels can be light levels of the light beams projected/sourced from the contact lens 102 or light that originates from the HUD and is reflected off the lens. In some aspects, the waveguide can be employed to direct light 110 from a light source 112 on the heads-up device 114 to the eye 104 covered by the contact lens 102. The reversed/reflected version of the light can be transmitted back to one or more sensors 120. For example, the light 110 can be reflected back to a complementary metal oxide semiconductor (CMOS)-based sensor or to a charge-coupled device (CCD)-based sensor on the heads-up device 114.

The VCSEL on the contact lens 102 can generate information 118 that is used to determine gaze of the eye 104 on which the lens 102 is worn. The VCSEL can scan out/output the information 118 about the gaze to the one or more sensors 120 (e.g., CMOS-based sensor or CCD-based sensor) on the heads-up device 114. In various aspects, the sensor 120 can be included in an image generation portion (not shown) of the heads-up device 114.

The VCSEL can also output infrared (IR) light in some aspects. The mode of operation only differs in this aspect (relative to the aspect in the preceding paragraph) in that the IR light is not coupled into a waveguide, but, instead, is reflected off an object at which the user is gazing. The reflected light is then collected by the camera.

While the above-referenced aspects described waveguides and cameras on the heads-up device 114, in some aspects, the heads-up device 114 can be a pair of glasses. In some aspects, one or more of the components of the heads-up device 114 can be formed on or integrated with the pair of glasses. The glasses can be worn by the wearer of the contact lens 102 and/or can display one or more images for viewing by the wearer of the contact lens 102.

In some embodiments, an IR source can be placed near an optics module of the heads-up device 114. The optics module can image the eye through the waveguide. The image information generated can be employed to perform eye tracking. In particular, eye tracking can be performed employing the IR source in at least two aspects that do not require a contact lens. A first aspect can facilitate tracking in low-light environments. For example, an IR source on a heads-up device 114 can emit light towards the eye of a person in proximity to the heads-up device 114, and sense the IR light reflected from the eye. In some aspects, the IR light reflections off the eye can be detected by the heads-up device 114 to determine direction of gaze of the person. Accordingly, in some aspects, determination of direction of gaze of a person can be made without reliance on a contact lens being worn by the person. However, in some aspects, a contact lens can be worn by the person. The contact lens can then be employed as an alignment mark or a fiduciary marker.

Second, an IR source on the heads-up device 114 can emit light that passes through the waveguide of the heads-up device 114. The direction of gaze of a person in proximity to the heads-up device 114 can be determined by a hybrid projector/camera system on the heads-up device 114. In some aspects, the camera of the hybrid projector/camera system can be in addition to a camera that faces the world outside of the person (which can be employed for projecting images for the viewer).

In some aspects, the circuit 106 can communicate information 108 to a reader 116. For example, the information 108 can include, but is not limited to, information indicative of telemetry and/or the position of the eye over which the contact lens 102 is placed. In some aspects, the reader 116 can be a radio frequency (RF) reader.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received or transmitted data.

In various aspects, information obtained from eye tracking can be employed in any number of different contexts including, but not limited to, controlling a user interface (UI) (e.g., in lieu of operating a mouse to control the UI, eye movements and/or positions can be employed to control the UI). Any number of different eye movements or positions can be determined and a device can be controlled based on the eye movement or position. For example, moving the eye from left to right (or right to left) can be indicative of selection of text; moving the eye up and down (or down and up) can be indicative of pressing the "Enter" button on a keypad. Looking into a far corner of the eye region can be indicative of exiting out of a program. The systems described herein can determine the type of movement or position of the eye, and perform a function to control an application or device based on the determined position and/or movement.

As shown in FIG. 1, in some aspects, the circuit 106 can receive power 122 from a power source component 124 of the heads-up device 114. For example, power 122 can be received from a radio frequency (RF) power source. In some aspects, solar power can be generated based on light from a solar power source (not shown) or via ambient light.

Figure 2A:
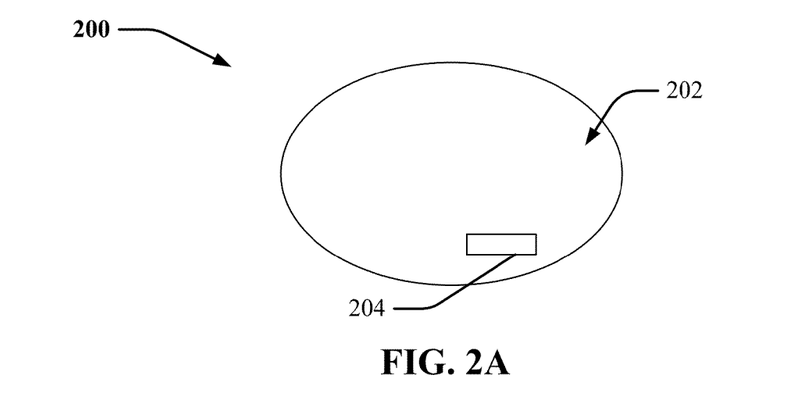
FIG. 2A is a top-view illustration of an exemplary non-limiting contact lens that facilitates eye tracking in accordance with aspects described herein.
Figure 2B:
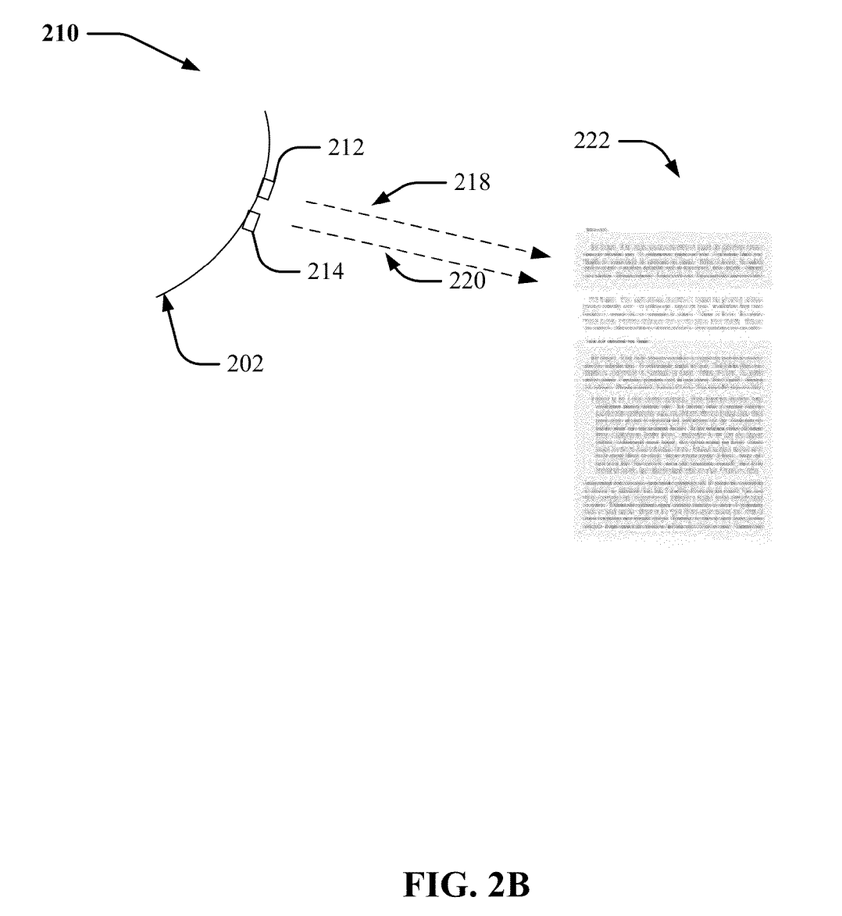
FIG. 2B is a side-view illustration of an exemplary non-limiting contact lens that facilitates performance of eye tracking in accordance with aspects described herein.
Figure 3:
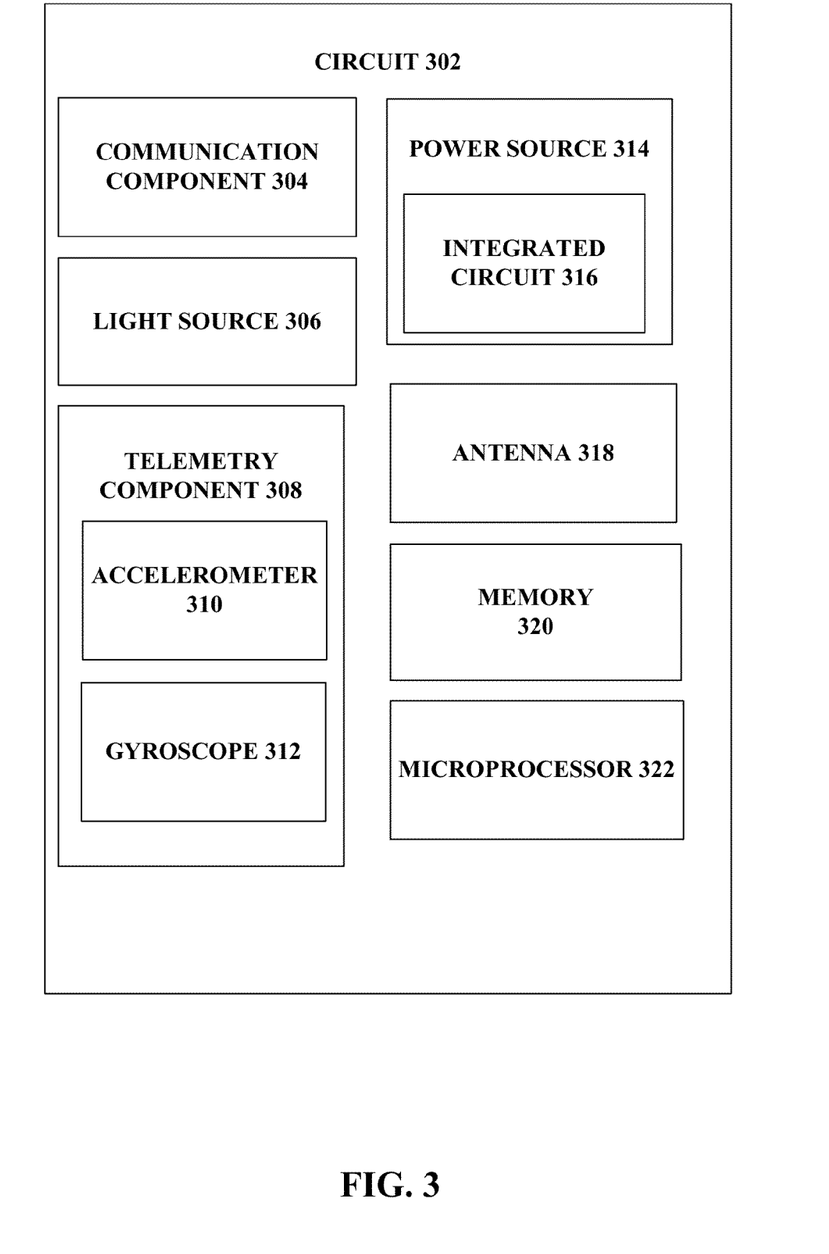
FIG. 3 is an illustration of an exemplary non-limiting block diagram for a circuit that facilitates eye tracking employing a contact lens in accordance with aspects described herein.

The contact lens 102 and circuit 106 will be described in greater detail with reference to FIGS. 2A, 2B and/or 3. FIG. 2A is a top-view illustration of an exemplary non-limiting contact lens that facilitates eye tracking in accordance with aspects described herein. FIG. 2B is a side-view illustration of an exemplary non-limiting contact lens that facilitates eye tracking in accordance with aspects described herein. FIG. 3 is an illustration of an exemplary non-limiting block diagram for a circuit that facilitates eye tracking employing a contact lens in accordance with aspects described herein.

Turning first to FIG. 2A, the contact lens 200 includes a substrate 202 having a circuit 204 disposed on or within the substrate 202. The circuit 204 can perform and/or facilitate eye tracking in various aspects. A number of these aspects are as described in greater detail with reference to FIG. 1. For example, the circuit 204 can determine the motion of the eye over which the contact lens 200 is disposed and perform telemetry-based eye tracking based on the motion of the eye. As another example, the circuit 204 can provide one or more light beams that can radiate from the contact lens. The direction of the one or more light beams can be employed (e.g., by a heads-up device in geographic proximity to the wearer of the contact lens 200) to determine direction of gaze of the eye over which the contact lens 200 is disposed.

FIG. 2B illustrates a contact lens 210 having a substrate 202 and one or more light emitters 212, 214. The light emitters 212, 214 can be substantially fixed in position on or within the substrate 202. As such, the light emitters 212, 214 can move in conjunction with the contact lens 210 in a direction corresponding to direction of the pupil of the eye. As such, the light emitters 212, 214 can radiate light beams 218, 220 in a direction corresponding to direction of gaze of the wearer of the contact lens 210.

A heads-up device (not shown) can determine direction of gaze based on direction of the light beams 218, 220 employing a camera or other device, as described with reference to FIG. 1.

In some aspects, the heads-up device can project an augmented piece of information relating to a location on which the light beams 218, 220 fall. For example, in some aspects, the location on which the light beams 218, 220 fall includes page 222 of a book. In some aspects, for example, the heads-up device can determine that a wearer of the contact lens 210 is reading line 20 on page 222. If the wearer should look away, upon resumption of reading the page 222, the heads-up device can project an indicator that the wearer of the contact lens 210 stopped reading the page 222 at line 20. For example, the indicator can be a beam of colored light emitted from the heads-up device and that is directed to line 20.

Turning now to FIG. 3, in some aspects, the circuit 302 of one or more contact lenses described herein can include one or more of the following components: a communication component 304, a light source 306, a telemetry component 308, a power source 314, an antenna 318, memory 320 and/or a microprocessor 322. In various aspects, one or more of the communication component 304, light source 306, telemetry component 308, power source 314, antenna 318, memory 320 and/or microprocessor 322 can be electrically, optically and/or communicatively coupled to one another to perform one or more functions of the circuit 302.

The communication component 304 can transmit information from and/or receive information at the circuit 302. In various aspects, the information transmitted can be information about the position and/or motion of the eye over which the contact lens is worn, telemetry information or the like. In some aspects, the communication component 304 can transmit the information to a reader external to the contact lens (e.g., reader 116 described with reference to FIG. 1) or to a heads-up device (e.g., heads-up device 114 described with reference to FIG. 1).

In various aspects, the circuit 302 can include one or more light sources, such as light source 306. Light source 306 can be disposed on or within the substrate of the contact lens and faced away from the eye such that the light source can radiate a light beam into an environment outside of the wearer of the contact lens. In some aspects, as the contact lens moves with the eye, the light source 306 moves with the direction of gaze of the eye.

The light source 306 can vary in wavelength and/or emission mechanism. For example, the light source 306 can be or include a light-emitting diode with a lens mechanism to restrict beam width and/or a VCSEL for more direct gaze lines, and as discussed with reference to FIG. 1.

In various aspects, the wavelength of the light radiated from the light source 306 can be in the IR range. Accordingly, the light can be invisible to the human eye but detectable at a light detector (e.g., optics module) on a heads-up device external to the contact lens.

As shown, the circuit 302 can also include a telemetry component 308. The telemetry component 308 can determine the motion of an eye over which the contact lens is placed and/or perform eye tracking based on the motion. In some aspects, the telemetry component 308 can include an accelerometer 310 and/or a gyroscope 312. The accelerometer 310 and gyroscope 312 can be fixed in position on the contact lens, and can be employed to determine motion of the eye on which the contact lens is placed. For example, the accelerometer 310 can determine acceleration of eye movement and the gyroscope 312 can determine angular displacement of the eye. The angular displacement information can be collected and the set of data employed to determine absolute position of the eye. In various aspects, the accelerometer 310 and/or gyroscope can record (or be employed in recording) the motion of the eye.

The telemetry component 308 can employ signal time of flight, amplitude shifts, and/or offsets in the operational frequency to track a position of the eye. For example, the signal time of flight can be the time for a signal (e.g., optical signal) to travel from a transmitter to a receiver. The travel time is a measure of the distance between the transmitter and the receiver. The distance can be employed in determining position (or orientation) of the eye in some aspects.

In various aspects, the antenna 318, integrated circuit (IC) 316, accelerometer 310 and/or gyroscope 312 can be fabricated on the contact lens according to microfabrication processes.

The antenna 318 can be included in the communication component 304 in some aspects. The antenna 318 can communicate information indicative of movement and/or position of the eye over which the contact lens is disposed. For example, the antenna 318 can communicate with the RF reader 116 referenced with regard to FIG. 1.

In various aspects, the information can be wirelessly transmitted to a reader or a heads-up device in geographic proximity to the contact lens. For example, the heads-up device can include a radio system that can transmit and/or receive signals to or from the circuit 302 on the contact lens.

In various aspects, the information transmitted by the antenna 318 can be communicated based on the strength of the signal carrying the information. For example, the signal transmitted from the antenna 318 can vary in strength depending on the position of the eye. For example, to communicate a first position of the eye, the signal transmitted from the antenna 318 can be a first signal strength. To communicate a second position of the eye, the signal transmitted from the antenna 318 can be a second signal strength. The radio system of the heads-up device, or the RF reader, can be configured to determine the position of the eye based on the signal strength received.

In some aspects, the antenna 318 can be or be included within a multi-antenna system (not shown). The multi-antenna system can increase the reliability and accuracy of the information transmitted from or received at the contact lens. For example, an RF signal can be transmitted from a heads-up device to a multi-antenna system on the contact lens. The multi-antenna system can receive the RF signal and the signal strength of the received signal can be measured at the antennas of the multi-antenna system as the signal received by each antenna will have orientation dependence. Accordingly, depending on the direction the gaze of the eye, a particular antenna may have a stronger response to the signal than the response of the other antennas of the multi-antenna system. Evaluating strength of signals received at different antennas, orientation of the contact lens can then be inferred. The position of the eye over which the contact lens is disposed can be determined based on orientation of the contact lens.

Accordingly, in some aspects, direction of gaze of the eye can be determined based on signal strength information at a multi-antenna system on the contact lens. In other aspects, direction of gaze can be determined based on direction of light beams radiating from the contact lens, as described above. In other aspects, position of the eye can be determined based on telemetry components on the contact lens.

Accordingly, in some aspects, multiple light sources can emit light beams from the contact lens, and in other aspects, multiple light sources can emit light beams from the heads-up device. These light beams can be differentiated from one another to facilitate determination of position or orientation of the eye.

Turning back to antenna 318, in some aspects, the antenna 318 can be included as part of the power source 314. For example, the antenna 318 can harvest RF energy for use by one or more components of the circuit 302. The RF energy can be received from the environment surrounding the antenna 318 in some aspects.

Further, in some aspects, the power source 314 can include an integrated circuit (IC) 316 that can receive, process and/or distribute power from the antenna 318. The power source 314 can provide power to the light source 306, communication component 304, telemetry component 308, memory 320 and/or microprocessor 322 in various aspects.

The memory 320 can be a computer-readable storage medium storing computer-executable instructions and/or information for performing the functions described in this disclosure with reference to the circuit 302, in particular and/or any of the aspects of the contact lens, in general. In some aspects, the memory 320 can store information including, but not limited to, eye position information, eye motion information, measurements from the accelerometer and/or gyroscope or the like.

The microprocessor 322 can perform one or more of the functions described in this disclosure with reference to the circuit 302 (or components thereof), in particular and/or any of the aspects of the contact lens, in general.

While FIG. 3 displays circuit 302 with the components illustrated and/or described, in some aspects, the circuit 302 can include a subset of the components. For example, in one aspect, the contact lens can include a circuit that includes at least one light source (light source 306), in another aspect, the contact lens can include a circuit that includes telemetry component 308. Numerous different aspects can be envisaged employing one or more of the components shown in circuit 302. All such aspects are encompassed by the disclosure.

Figure 4:
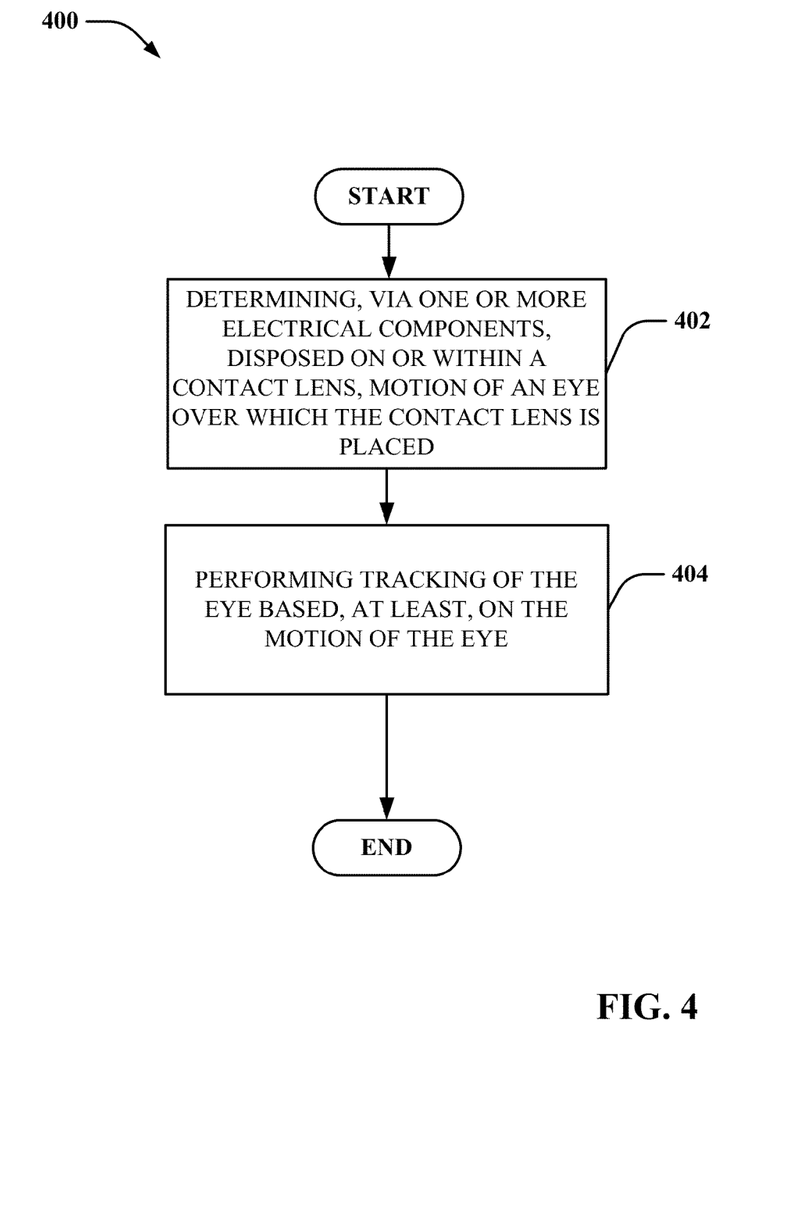
FIGS. 4, 5, 6 and 7 are illustrations of exemplary flow diagrams of methods that facilitate eye tracking employing a contact lens in accordance with aspects described herein.

FIGS. 4, 5, 6 and 7 are illustrations of exemplary flow diagrams of methods that facilitate eye tracking employing a contact lens in accordance with aspects described herein. Turning first to FIG. 4, at 402, method 400 can include determining, via one or more electrical components disposed on or within a contact lens, motion of an eye over which the contact lens is placed (e.g., using the accelerometer 310 or the gyroscope 312). For example, as described, motion can be determined employing an accelerometer 310 disposed on the contact lens or employing a determination of directions of one or more light beams radiating from the contact lens.

At 404, method 400 can include performing tracking of the eye based, at least, on the determining of the motion of the eye (e.g., using the telemetry component 308). For example, the circuit on the contact lens can determine acceleration or position of the eye and generate corresponding telemetry indicative of the acceleration or position. The position of the eye can be tracked based on the current position of the eye for example.

Figure 5:
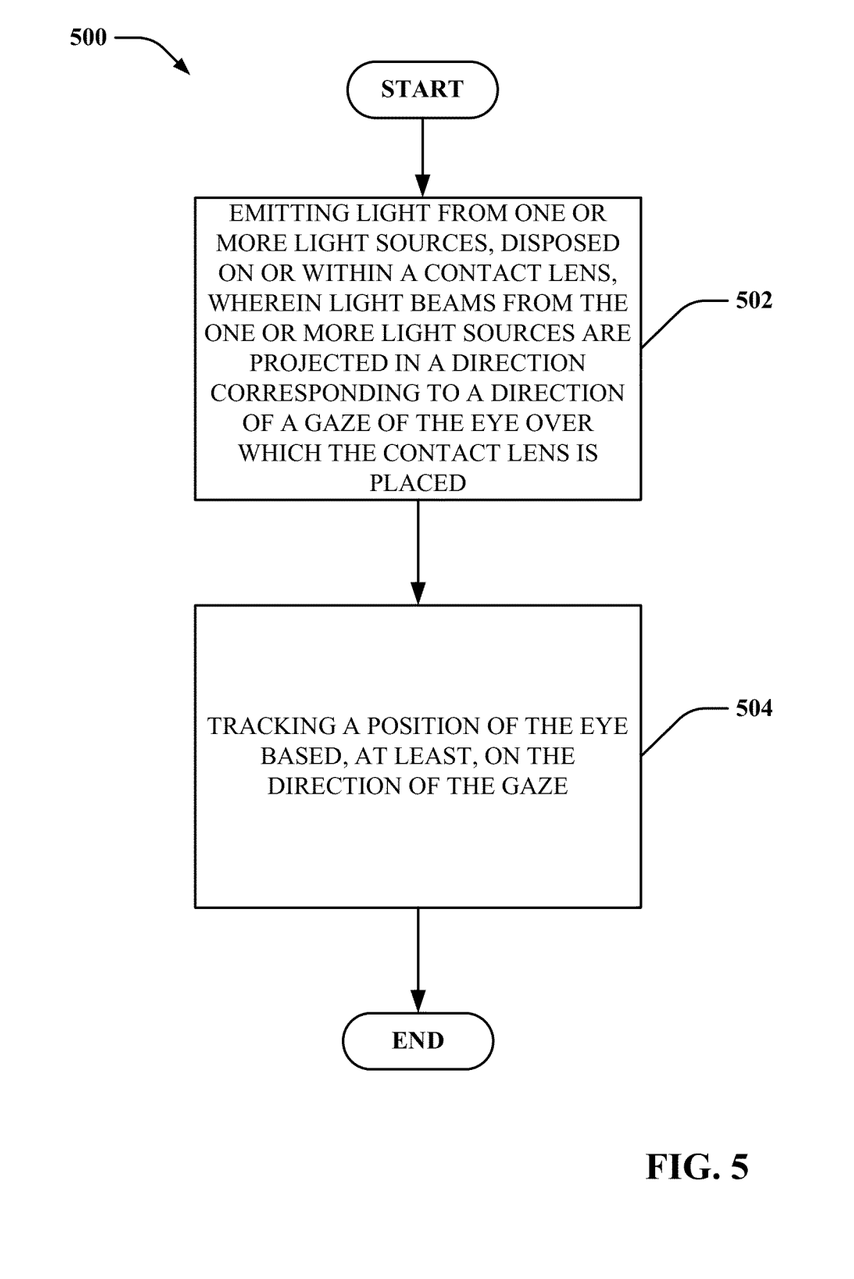

Turning now to FIG. 5, at 502, method 500 can include emitting light from one or more light sources disposed on or within a contact lens. The light beams from the light sources can radiate in a direction corresponding to direction of gaze of the eye over which the contact lens is placed (e.g., using the light source 306). For example, the light sources can be fixed in position on the contact lens. When the eye over which the contact lens is disposed moves, the light beams emitted from the light sources can correspondingly move.

At 504, method 500 can include tracking a position of the eye based, at least, on the direction of the gaze (e.g., using the heads-up device 114). The direction of the light beams can be tracked and the position of the eye determined based on the tracked light beams. For example, a heads-up device can determine a location on which the one or more light beams fall based on the direction of the light beams.

Although not shown, in some aspects, a VCSEL on the contact lens can reverse light transmitted to the contact lens through a waveguide on a heads-up device. The light from the contact lens can be transmitted to a sensor on the heads-up device (e.g., a CMOS-based sensor or a CCD-based sensor). The sensor can determine position of the eye based on the cells of the sensor on which the light is received. In various aspects, the sensor can be included in the image generation portion of the heads-up device 114.

In some aspects, a camera can be employed on the heads-up device 114 to display the information at which the wearer is gazing. For example, a camera on the heads-up device 114 can display a paragraph of a book at which the wearer is gazing.

Figure 6:
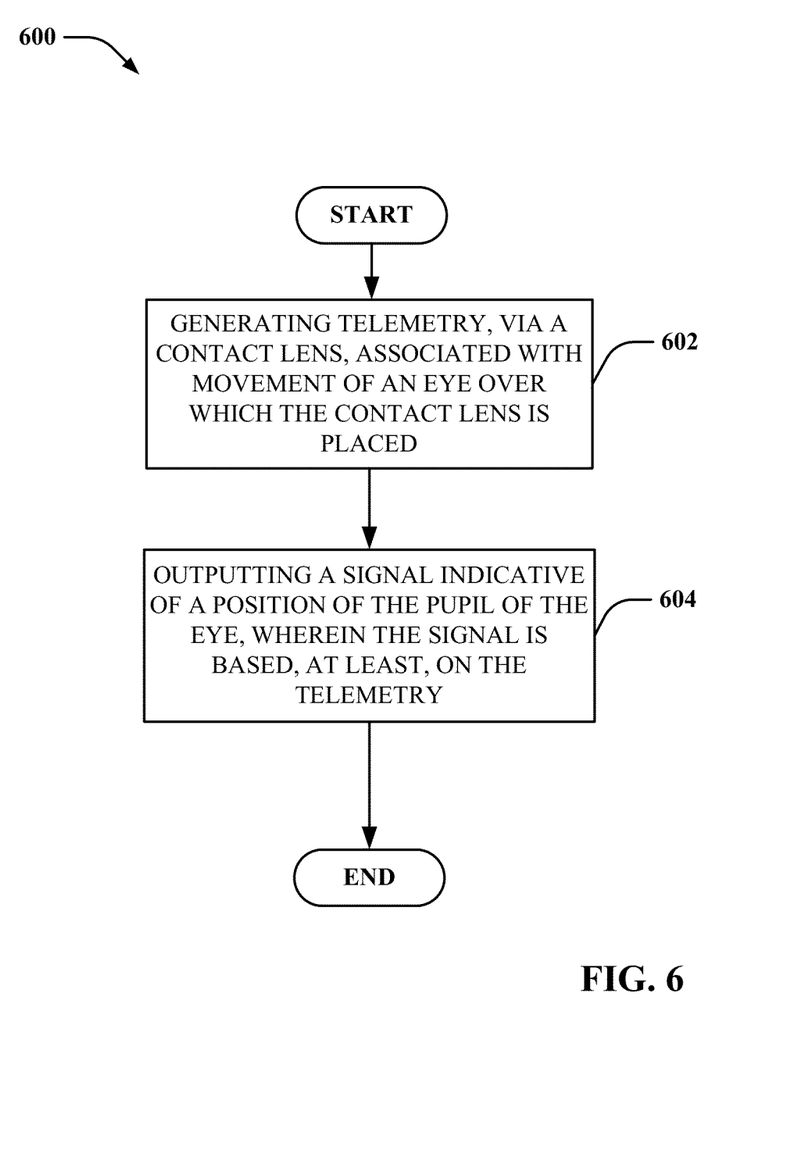

Turning now to FIG. 6, at 602, method 600 can include generating telemetry, via a contact lens, associated with movement of an eye over which the contact lens is placed (e.g., using the telemetry component 308).

At 604, method 600 can include outputting a signal indicative of a position of the pupil of the eye, wherein the signal is based, at least, on the telemetry (e.g., using the communication component 304).

Figure 7:
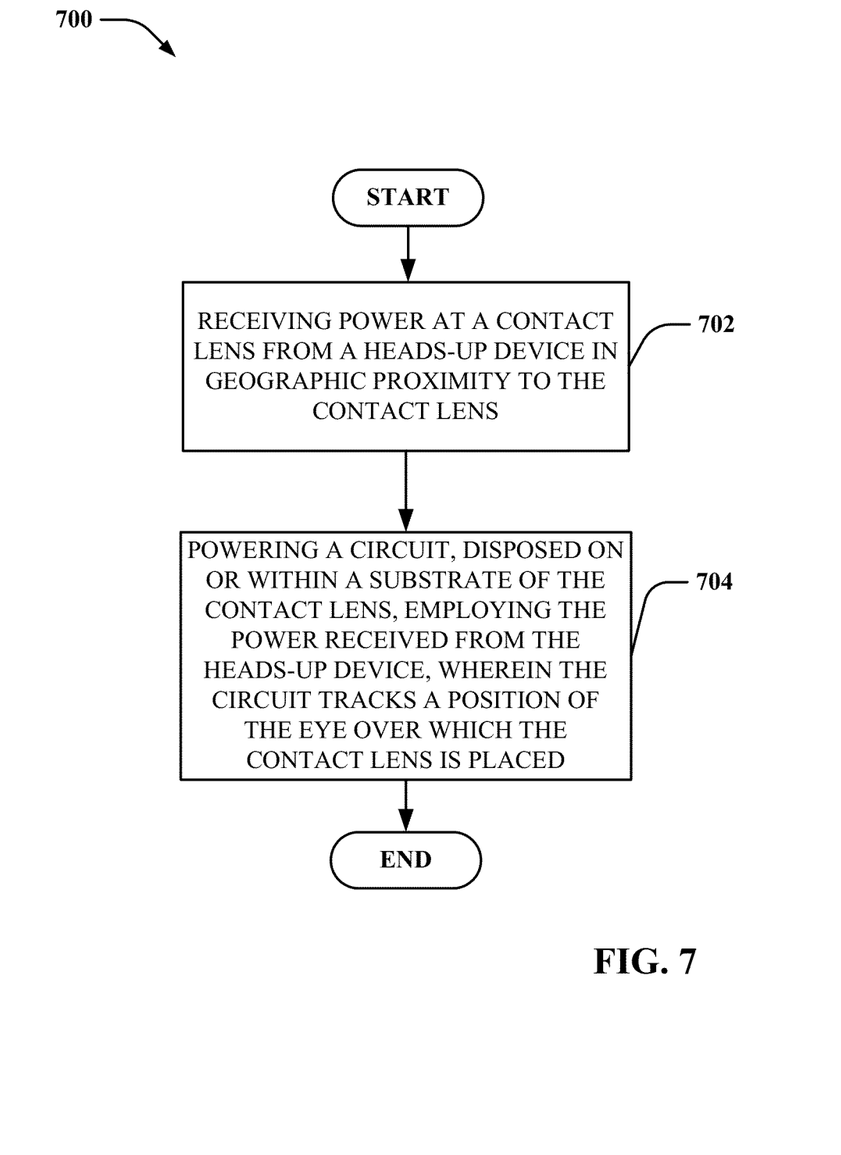

Turning now to FIG. 7, at 702, method 700 can include receiving power at a contact lens from a heads-up device in geographic proximity to the contact lens (e.g., using the antenna 318). For example, the heads-up device can include a power source (e.g., RF power source) that can emit RF waves. In other aspects, the heads-up device can include a solar power source (e.g., an artificial light source).

At 704, method 700 can include powering a circuit disposed on or within the substrate of the contact lens (e.g., using the power source 314). For example, the contact lens circuit can receive RF waves and generate RF power that can be employed in powering one or more components of the contact lens. The circuit can facilitate tracking of a position of the eye over which the contact lens is placed, emitting light to enable a heads-up device to determine the position of the eye or the like.

Exemplary Networked and Distributed Environments

Figure 8:
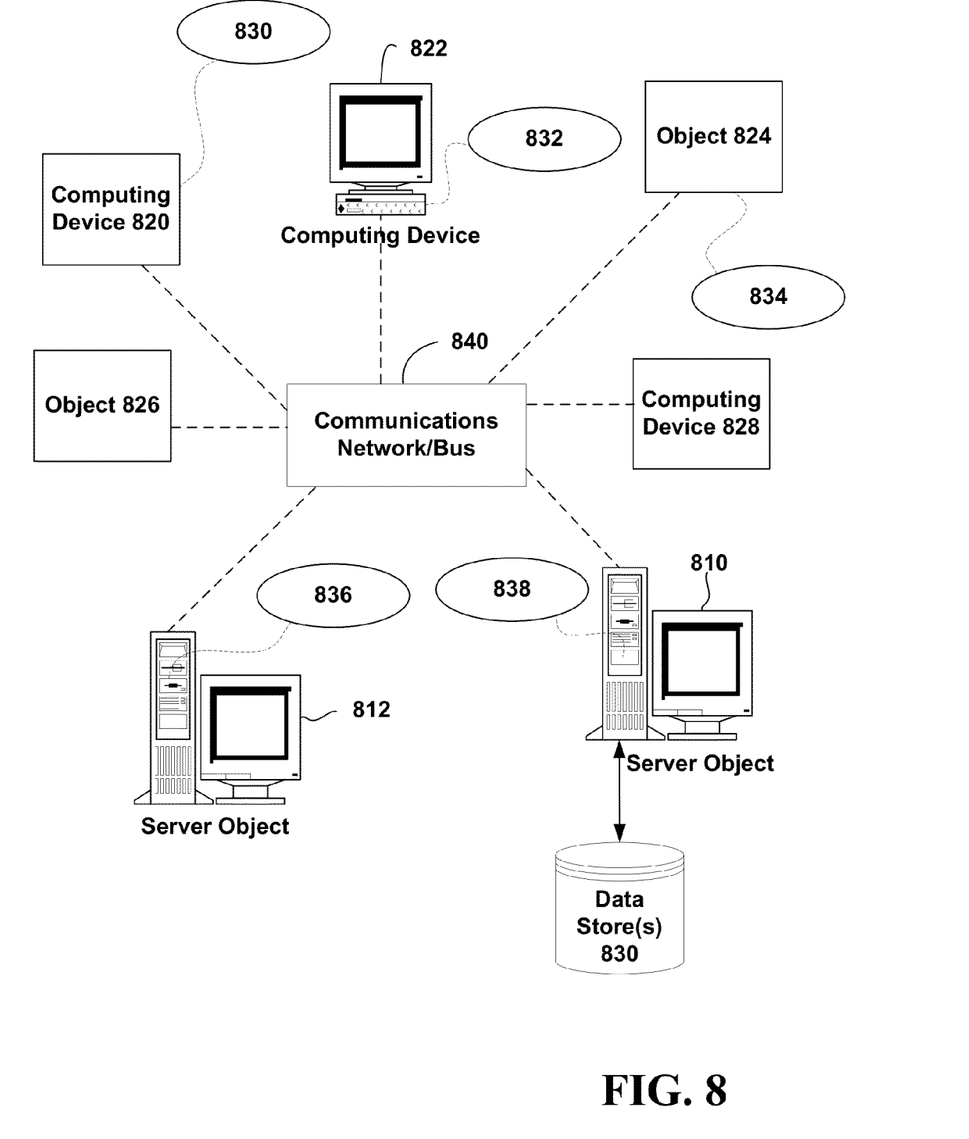
FIG. 8 is an illustration of a schematic diagram of an exemplary networked or distributed computing environment with which one or more aspects described herein can be associated.

FIG. 8 provides a schematic diagram of an exemplary networked or distributed computing environment with which one or more aspects described in this disclosure can be associated. The distributed computing environment includes computing objects 810, 812, etc. and computing objects or devices 820, 822, 824, 826, 828, etc., which can include programs, methods, data stores, programmable logic, etc., as represented by applications 830, 832, 834, 836, 838. It can be appreciated that computing objects 810, 812, etc. and computing objects or devices 820, 822, 824, 826, 828, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 810, 812, etc. and computing objects or devices 820, 822, 824, 826, 828, etc. can communicate with one or more other computing objects 810, 812, etc. and computing objects or devices 820, 822, 824, 826, 828, etc. by way of the communications network 840, either directly or indirectly. Even though illustrated as a single element in FIG. 8, network 840 can include other computing objects and computing devices that provide services to the system of FIG. 8, and/or can represent multiple interconnected networks, which are not shown.

In a network environment in which the communications network/bus 840 can be the Internet, the computing objects 810, 812, etc. can be Web servers, file servers, media servers, etc. with which the client computing objects or devices 820, 822, 824, 826, 828, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the RF reader described herein. In various aspects, the data store can be any repository for storing information transmitted to or received from the contact lens.

Figure 9:
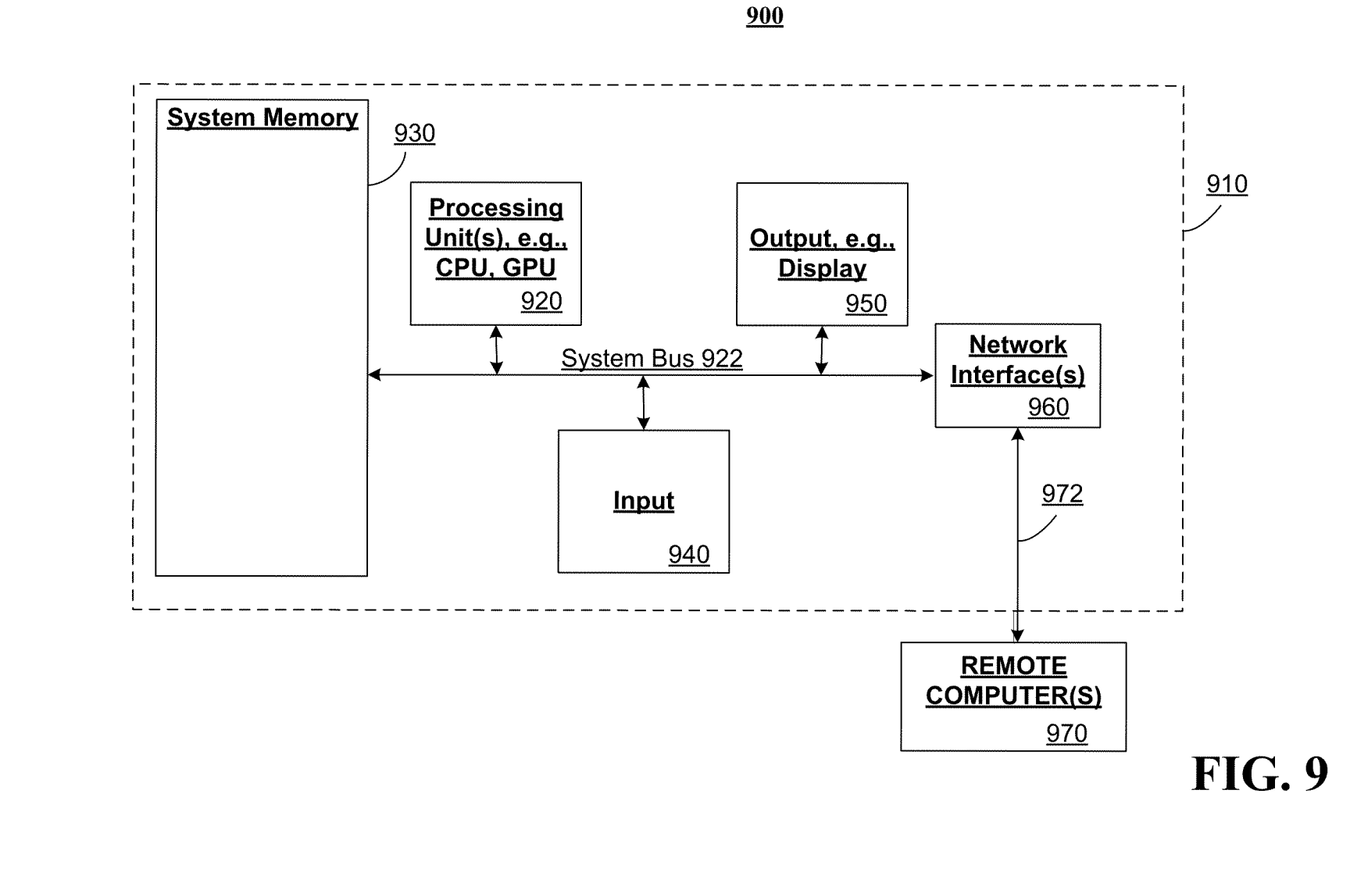
FIG. 9 is an illustration of a schematic diagram of an exemplary computing environment with which one or more aspects described herein can be associated.

FIG. 9 illustrates an example of a suitable computing system environment 900 in which one or aspects of the aspects described in this disclosure can be implemented. Components of computer 910 can include, but are not limited to, a processing unit 920, a system memory 930, and a system bus 922 that couples various system components including the system memory to the processing unit 920.

Computer 910 typically includes a variety of computer readable media and can be any available media that can be accessed by computer 910. The system memory 930 can include computer storage media in the form of volatile and/or nonvolatile memory such as read only memory (ROM) and/or random access memory (RAM). By way of example, and not limitation, memory 930 can also include an operating system, application programs, other program components, and program data.

A user can enter commands and information into the computer 910 through input devices 940 (e.g., keyboard, keypad, a pointing device, a mouse, stylus, touchpad, touch screen, motion detector, camera, microphone or any other device that allows the user to interact with the computer 910). A monitor or other type of display device can be also connected to the system bus 922 via an interface, such as output interface 950. In addition to a monitor, computers can also include other peripheral output devices such as speakers and a printer, which can be connected through output interface 950.

The computer 910 can operate in a networked or distributed environment using logical connections to one or more other remote computers, such as remote computer 980. The remote computer 980 can be a personal computer, a server, a router, a network PC, a peer device or other common network node, or any other remote media consumption or transmission device, and can include any or all of the elements described above relative to the computer 910. The logical connections depicted in FIG. 9 include a network 982, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/ or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A system, comprising:
   a heads-up device; and
   a contact lens, the contact lens comprising:
      a substrate; and
      a circuit, disposed on or within the substrate, and comprising:
         a telemetry component configured to determine motion of an eye over which the contact lens is positioned and perform eye tracking based on the motion of the eye; and
         a communication component comprising an antenna, wherein the communication component is configured to transmit information related to the eye tracking to the heads-up device.

2. The system of claim 1, wherein the telemetry component comprise at least one of an accelerometer or a gyroscope.

3. The system of claim 1, wherein the heads-up device further comprises a power source component, and wherein the circuit of the contact lens is configured to receive power from the power source component of the heads-up device.

4. The system of claim 3, wherein the power source component comprises a radio frequency (RF) power source, and wherein the circuit comprises an antenna configured to receive RF power from the RF power source.

5. A system, comprising:
   a contact lens configured to be worn by a wearer, the contact lens comprising:
      a substrate;
      one or more light sources, disposed on or within the substrate, configured to emit one or more light beams from the contact lens, wherein the one or more light beams are projected in a direction corresponding to a direction of a gaze of an eye over which the contact lens is positioned, and tracking of the eye is performed based, at least on the direction of the gaze of the eye; and
      a power source disposed on or within the substrate, operably coupled to the one or more light sources; and a heads-up device configured to be worn by the wearer of the contact lens, wherein the heads-up device includes a light detector configured to determine where on an external object the one or more light beams fall.

6. The system of claim 5, wherein the one or more light sources have one or more wavelengths or light levels.

7. The system of claim 5, wherein the one or more light sources comprise at least one of a light-emitting diode or an infrared light source.

8. The system of claim 5, wherein the light detector is configured to detect infrared wavelengths, and wherein the one or more light sources comprise at least one infrared light source.

9. The system of claim 5, wherein the power source comprises at least one of an antenna configured to capture radio frequency energy generated by the heads-up device or solar power from a solar power device.

* * * * *